United States Patent
Patrissi et al.

(10) Patent No.: US 7,534,394 B1
(45) Date of Patent: May 19, 2009

(54) POTENTIOMETRIC TITRATION METHOD FOR QUANTITATIVE DETERMINATION OF HYDROGEN PEROXIDE

(75) Inventors: Charles J. Patrissi, Newport, RI (US); Russell R. Bessette, Mattapoisett, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 757 days.

(21) Appl. No.: 11/183,311

(22) Filed: Jul. 11, 2005

(51) Int. Cl.
*G01N 27/02* (2006.01)
*G01N 27/413* (2006.01)
*G01N 31/16* (2006.01)
*G01N 31/18* (2006.01)

(52) U.S. Cl. .............. 422/81; 422/98; 422/63; 422/67; 422/68.1; 422/100; 436/135; 436/137; 436/174; 436/179

(58) Field of Classification Search ............ 422/81, 422/98, 63, 67, 68.1, 100; 436/135, 137, 436/174, 179
See application file for complete search history.

(56) References Cited

U.S. PATENT DOCUMENTS

| | | | |
|---|---|---|---|
| 3,403,081 A * | 9/1968 | Rohrback et al. | 205/777.5 |
| 3,526,578 A * | 9/1970 | Silverman | 205/778 |
| 3,595,755 A | 7/1971 | Hartel | |
| 4,003,705 A * | 1/1977 | Buzza et al. | 436/68 |
| 4,118,194 A * | 10/1978 | Raleigh et al. | 422/98 |
| 4,246,343 A * | 1/1981 | Wilkins et al. | 205/777.5 |
| 4,288,543 A * | 9/1981 | Sielaff et al. | 435/34 |
| 4,321,322 A * | 3/1982 | Ahnell | 205/777.5 |
| 4,386,157 A * | 5/1983 | Beggs et al. | 435/39 |
| 4,571,543 A * | 2/1986 | Raymond et al. | 324/425 |
| 4,576,916 A * | 3/1986 | Lowke et al. | 435/288.7 |
| 4,587,100 A | 5/1986 | Amano et al. | |
| 4,647,532 A | 3/1987 | Watanabe et al. | |
| 4,801,546 A * | 1/1989 | Ackland | 435/287.1 |
| 4,908,323 A | 3/1990 | Werner | |
| 4,933,277 A | 6/1990 | Abe et al. | |
| 5,254,461 A * | 10/1993 | Rohrback et al. | 205/777.5 |
| 5,474,938 A | 12/1995 | Jadesjo et al. | |
| 2002/0127144 A1* | 9/2002 | Mehta | 422/81 |

* cited by examiner

*Primary Examiner*—Brian R. Gordon
(74) *Attorney, Agent, or Firm*—James M. Kasischke; Jean-Paul A. Nasser; Michael P. Stanley

(57) ABSTRACT

An electrochemical potentiometric titration method that entails titration of a known volume of a catholyte containing an unknown amount of hydrogen peroxide in a titration cell having two electrodes, a platinum working electrode and a silver/silver chloride reference electrode. A known concentration of a titrant is added to the catholyte in the titration cell. Simultaneously, as the titrant is added the potential between the working electrode and the reference electrode is monitored. The point at which all of the hydrogen peroxide has been consumed is signaled when the cell potential changes abruptly. Since the concentration of the titrant is already known, the amount of titrant added (concentration multiplied by volume) is directly related to the amount of hydrogen peroxide consumed. The concentration of hydrogen peroxide is calculated from the volume of catholyte and the moles of hydrogen peroxide.

10 Claims, 3 Drawing Sheets

POTENTIOMETRIC TITRATION METHOD FOR QUANTITATIVE DETERMINATION OF HYDROGEN PEROXIDE

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER RELATED APPLICATIONS

Not applicable.

BACKGROUND OF THE INVENTION (1) Field of the Invention

The present invention relates to titration methods, and more specifically to a potentiometric titration method for a quantitative determination of hydrogen peroxide.

(2) Description of the Prior Art

There continues to be a need for energy sources with a high energy density. In particular, there is a need for high energy density energy sources that can power unmanned undersea vehicles. Such energy sources when used to power such vehicles are required to have high energy density for long duration and quiet operation. Additionally, they must be relatively inexpensive, environmentally friendly, safe to operate, reusable, capable of a long shelf life and not prone to spontaneous chemical or electrochemical discharge.

The zinc silver oxide (Zn/AgO) electrochemical couple has served as a benchmark energy source for undersea applications. Because of its low energy density, however, it is not suitable for unmanned undersea vehicles whose energy density requirements are seven times those of the Zn/AgO electrochemical couple.

In an effort to fabricate power sources for unmanned undersea vehicle with increased energy density (over zinc-based power sources), research has been directed towards semi fuel cells (as one of several high energy density power sources being considered). Semi fuel cells normally consist of a metal anode, such as magnesium (Mg) and a catholyte such as hydrogen peroxide ($H_2O_2$). In general the performance and health of these types of semi fuel cells are a function of the quantity of hydrogen peroxide in the catholyte. The key to achieving a high energy density for these types of semi fuel cells lies in the efficient usage of the hydrogen peroxide. The electrochemical processes during cell discharge are:

Anode: $Mg \rightarrow Mg^{2+} + 2e^-$

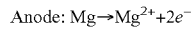

Cathode: $H_2O_2 + 2H^+ + 2e^- \rightarrow 2H_2O$

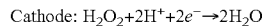

The voltage at the cathode and the total semi fuel cell voltage are directly related to the concentration of hydrogen peroxide in the catholyte according to the Nernst equation:

$$E = E^0 + (0.0591 * \log([H_2O_2] * [H^+]^2))/2$$

where E is the half cell voltage at the cathode, $E^0$ is the standard voltage at unit activity of $H_2O_2$ and $H^+$, and $[H_2O_2]$ and $[H^+]$ are the molar concentrations of peroxide and protons respectively. The Nernst equation shows that as the peroxide concentration decreases so does the cell voltage.

It is important to directly monitor and control the hydrogen peroxide concentration $[H_2O_2]$, because the concentration is used to assess the functional condition and performance of the semi-fuel cell. For example, if the hydrogen peroxide concentration differs significantly from expected levels for a given semi fuel cell load, then the pump controlling the hydrogen peroxide input can be directed to increase or decrease the amount of hydrogen peroxide being pumped into the semi fuel cell.

In a laboratory environment, measurement of hydrogen peroxide concentration in a semi fuel cell is performed using a calorimetric titration method. In this method, a solution of unknown peroxide concentration is colored with a small amount of indicator material such as iron(II) 1,10 phenanthroline. Then, a chemical of known concentration, typically cerium (IV) in sulfuric acid solution, (the titrant solution) is added that reacts with peroxide. When the solution turns clear, all of the hydrogen peroxide has been consumed. There is a 2:1 correlation between the number of titrant reactant molecules consumed during the titration and the number of hydrogen peroxide molecules initially present in the solution when cerium (IV) is used. The concentration of hydrogen peroxide can be determined using this correlation. This method is not suitable for use in an unmanned undersea vehicle, however, because it requires visible detection of a color change by a human operator. Currently there is no automated means for quantifying the concentration of hydrogen peroxide in a semi fuel cell onboard an unmanned undersea vehicle.

What is needed is a method of quantifying the concentration of hydrogen peroxide in a semi fuel cell catholyte that is automated and can provide concentration data that can be interpreted by a digital processor.

SUMMARY OF THE INVENTION

It is a general purpose and object of the present invention to establish a method of quantifying the concentration of hydrogen peroxide in a semi fuel cell catholyte that is automated and can provide concentration data that can be interpreted by a computer.

This object is accomplished by employing an electrochemical potentiometric titration method. The method entails titration of a known volume of a catholyte containing an unknown amount of hydrogen peroxide in a titration cell having two electrodes, a platinum working electrode and a silver/silver chloride reference electrode. A known concentration of a titrant is added to the known volume of catholyte in the titration cell. Simultaneously, as the titrant is added the potential between the working electrode and the reference electrode is monitored. The point at which all of the hydrogen peroxide has been consumed is signaled when the cell potential changes abruptly. Since the concentration of the titrant is already known, the amount of titrant added (concentration multiplied by volume) is directly related to the amount of hydrogen peroxide consumed. The concentration of hydrogen peroxide is calculated from the volume of catholyte and the moles of hydrogen peroxide.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
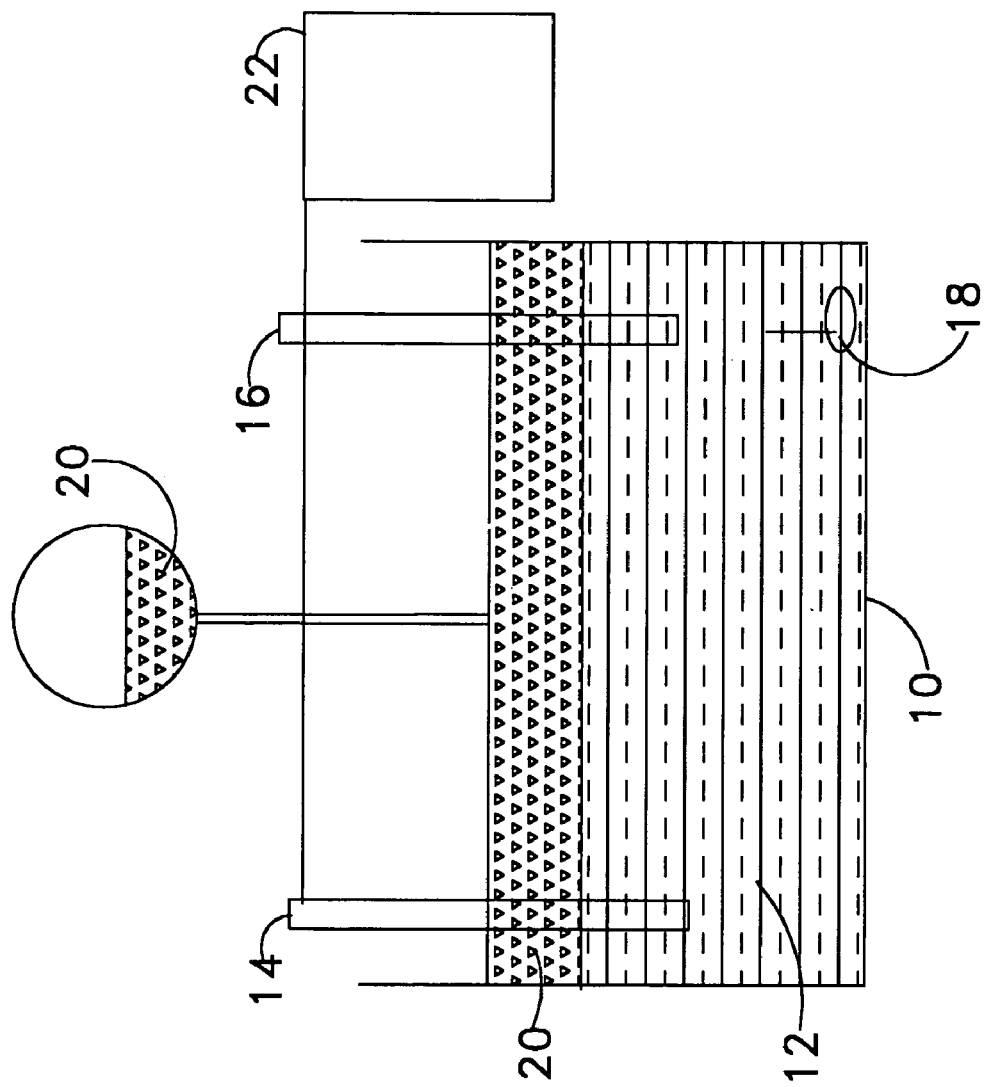
FIG. 1 is a diagram illustrating the apparatus of the present invention.

Referring now to FIG. 1 there is illustrated a diagram of the invention where an electrochemical titration cell 10 contains a certain volume of catholyte 12. Inside the titration cell 10 are two electrodes, working electrode 14 and reference electrode 16. Also contained inside the titration cell is a mechanical stir bar 18. In the preferred embodiment, the titration cell will be relatively small to conserve volume when used onboard an unmanned undersea vehicle. In the preferred embodiment, the working electrode 14 is made of platinum, and the reference electrode 16 is made of silver/silver chloride. A titrant solution 20 is introduced into the titration cell 10. In the preferred embodiment, the titrant solution 20 is a solution of $Ce^{4+}$. The potential between the working electrode and the reference electrode is measured once the titrant solution 20 is introduced. In the preferred embodiment, the potential is measured by means of a potentiostat/galvanostat 22.

The chemical reactions occurring in the titration cell are shown in Equations 1-3:

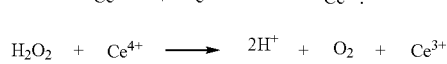

The addition of $Ce^{4+}$ into the catholyte oxidizes the hydrogen peroxide. During the addition of $Ce^{4+}$, the cell potential will be controlled by the $H_2O_2/O_2$ redox couple. Immediately following consumption of all the peroxide, the cell potential will shift to that of the $Ce^{4+}/Ce^{3+}$ redox couple. This abrupt change in the cell potential signals the end point of the titration and can be used by a computer to calculate the molarity of the hydrogen peroxide.

Figure 2:
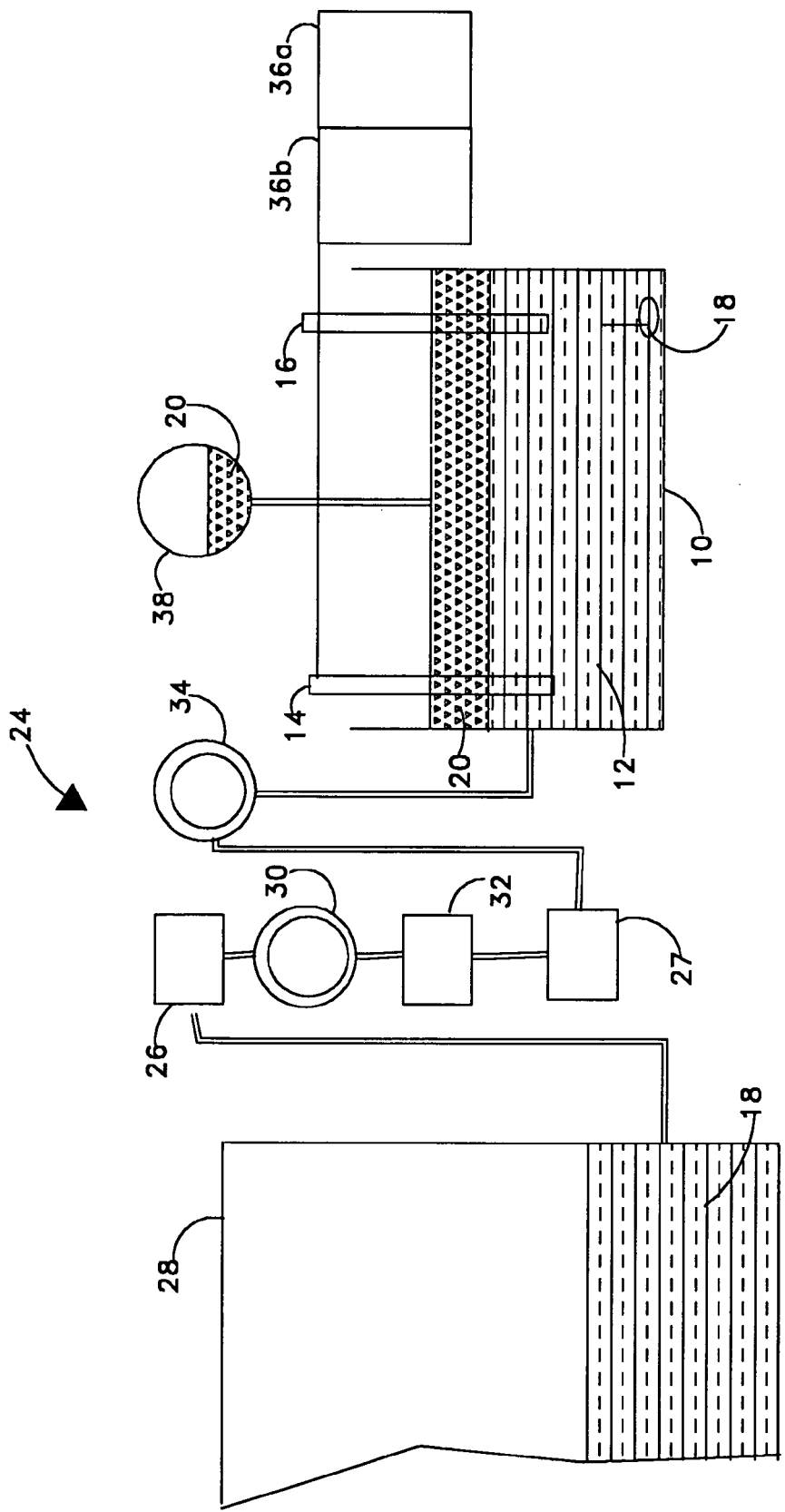
FIG. 2 is a diagram illustrating flow injection analysis system of the present invention.
Figure 3:
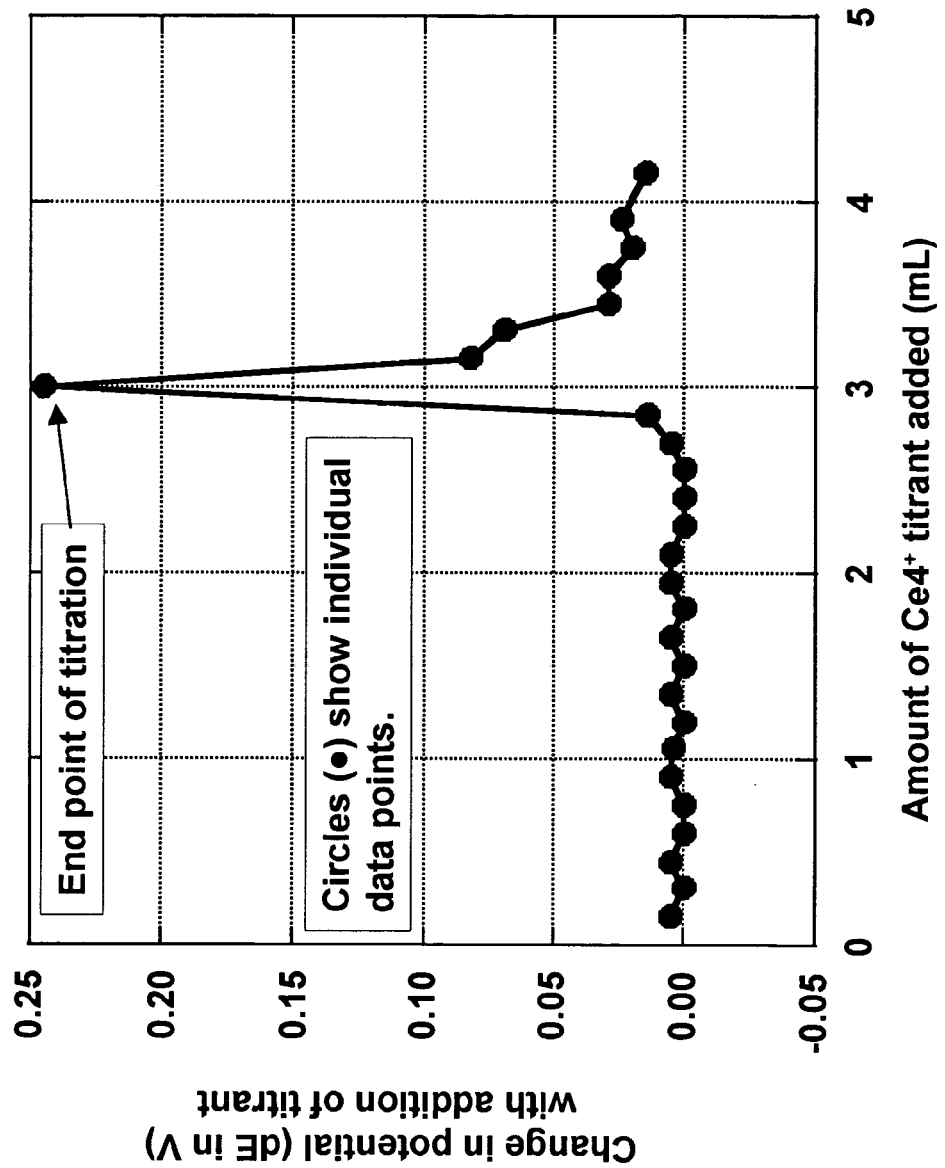
FIG. 3 is a graph of dE/dV versus titrant as recorded by the injection analysis system of the present invention.

In a preferred implementation of the invention, a flow injection analysis system 24 is used for on-line analysis as illustrated in FIG. 2. A micro-pump 26 will be connected to the catholyte chamber 28 of a semi fuel cell. The micro-pump 26 will remove a small fixed volume of catholyte and fill a fixed volume sample loop 30. The loop 30 empties into a dilution chamber 32 containing a known volume of electrolyte that does not contain $H_2O_2$ to dilute the small fixed volume of catholyte. A micro-pump 27 will then fill a second fixed volume sample loop 34 with the diluted sample of the catholyte. This diluted sample will be emptied into a titration cell 10 containing the reference electrode 16 and the working electrode 14. The electrodes are connected to a combined programmable digital processing unit 36a and high impedance voltmeter 36b. The digital processing unit 36a also controls a micro-burette 38 that introduces the titrant into the titration cell 10 at a fixed rate as a stirring device 18 mixes the titrant and diluted sample. The digital processing unit 36a receives the readings from the voltmeter 36b and performs the calculation dE/dV, where dE is the change in cell potential and dV is the change in volume of titrant from the previous data point. The endpoint of the titration is signaled when the slope of this graph changes from positive to negative as illustrated in FIG. 3. At this point the digital processing unit 36a is programmed to stop the micro-burette 38 from introducing any more titrant into the titration cell 10. Based on the volume of titrant that was delivered up to the endpoint, and because all of the volumes are fixed, the digital processing unit 36a is programmed to calculate the concentration of hydrogen peroxide in the original catholyte sample.

In a laboratory experiment, 20 micro liters of catholyte was diluted to 20 milliliters in a 50-milliliter dilution chamber containing 40 g/L of sodium chloride. The $H_2O_2$ concentration in the catholyte was determined to be 0.105 moles per liter using the colorimetric cerium (IV) titration method. The diluted catholyte was then placed in a titration cell and the cell potential was measured. A $Ce^{4+}$ titrant solution that was 0.001366 M was then titrated into a titration cell and the cell potential was measured 45 seconds after each addition of titrant. A graph of dE/dV versus titrant added is illustrated in FIG. 3. The graph shows the sharp change in dE/dV at 3.00 milliliters, which is the end point of the titration. The calculation of the hydrogen peroxide molarity is as follows:

(0.00300 L of $Ce^{4+}$)*(0.001366 moles of $Ce^{4+}$/one liter of $Ce^{4+}$ solution)*(1 mole $H_2O_2$/2 moles $Ce^{4+}$)/20×10$^{-6}$ L of catholyte=0.102 moles of $H_2O_2$ per liter of solution.

The error of the measurement is acceptable at 2.9%.

The advantages of the present invention over the prior art are autonomous/automated control of hydrogen peroxide, $H_2O_2$, concentration to assess the functional condition (health) and performance of a hydrogen peroxide, $H_2O_2$, based fuel cell.

Obviously many modifications and variations of the present invention may become apparent in light of the above teachings. For example they include various reference electrodes such as the saturate calomel electrode, various non corroding electrode materials such as gold or palladium, various dilution ratios depending on titration cell volume, expected peroxide concentration, etc, various types of electronic instrumentation to perform the measurement and acquire and process the data, and different analysis methods to determine the endpoint such as second derivative plot.

In light of the above, it is therefore understood that within the scope of the appended claims, the invention may be practiced otherwise than as specifically described.

What is claimed is:

1. A flow injection analysis apparatus for determining the concentration of hydrogen peroxide in a solution contained in a chamber, comprising: a chamber containing said solution;
   a means for removing a sample of solution from said chamber;
   a first fixed volume sample loop connected to said means for removing a sample of solution, to receive said sample of solution;
   a dilution chamber containing a known volume of an electrolyte connected to said first fixed volume sample loop to receive and dilute said sample of solution;
   a means for removing a sample of diluted solution from said dilution chamber;
   a second fixed volume sample loop connected to said means for removing a sample of diluted solution, to receive the sample of diluted solution;
   a titration cell containing a reference electrode, a working electrode, and a means for stirring a liquid, said titration cell being connected to said second fixed volume sample loop to receive the sample of diluted solution;

a voltmeter connected to said reference electrode and working electrode to perform periodic measurements of the titration cell potential;

a programmable digital processing unit connected to said voltmeter, wherein said digital processing unit receives the periodic measurements of the titration cell potential from the voltmeter; and a means for introducing a volume of titrant into the titration cell at a fixed rate, said means being connected to and controlled by said digital processing unit, wherein said digital processing unit performs a plurality of calculations of the differential in titration cell potential expressed as $dE/dV$, where E is the titration cell potential and V is the volume of titrant, such that when the differential in titration cell potential changes abruptly the digital processing unit stops the means for introducing a volume of titrant into the titration cell from introducing any more titrant into the titration cell and then calculates the concentration of hydrogen peroxide in the sample of solution.

2. An apparatus in accordance with claim 1 wherein said means for removing a sample of solution from said chamber comprises a first micro-pump connected to said chamber.

3. An apparatus in accordance with claim 1 wherein said means for removing a sample of diluted solution from said dilution chamber comprises a second micro-pump connected to the dilution chamber.

4. An apparatus in accordance with claim 1 wherein said reference electrode is composed of silver/silver chloride.

5. An apparatus in accordance with claim 1 wherein said working electrode is composed of platinum.

6. An apparatus in accordance with claim 1 wherein said means for stirring a liquid comprises a mechanical stirring bar.

7. An apparatus in accordance with claim 1 wherein said voltmeter is a high impedance voltmeter.

8. An apparatus in accordance with claim 1 wherein said voltmeter and said programmable digital processing unit are combined in the same electronic component.

9. An apparatus in accordance with claim 1 wherein said a means for introducing a volume of titrant into the titration cell at a fixed rate comprises a micro-burette.

10. The apparatus of claim 1, wherein the solution is a liquid catholyte solution and said chamber is a catholyte chamber of a semi fuel cell.

* * * * *